United States Patent [19]

Hartlaub et al.

[11] Patent Number: 4,493,325
[45] Date of Patent: Jan. 15, 1985

[54] TACHYARRHYTHMIA PACER

[75] Inventors: Jerome T. Hartlaub, New Brighton; Paul J. Beckmann, St. Paul, both of Minn.

[73] Assignee: Medtronic, Inc., Minneapolis, Minn.

[21] Appl. No.: 374,457

[22] Filed: May 3, 1982

[51] Int. Cl.³ .............................................. A61N 1/36
[52] U.S. Cl. .............................................. 128/419 PG
[58] Field of Search ..... 128/419 PG, 419 D, 705–706

[56] References Cited

U.S. PATENT DOCUMENTS

| | | | |
|---|---|---|---|
| 3,608,545 | 9/1971 | Novack et al. | 128/705 |
| 3,699,949 | 10/1972 | O'Hanlon, Jr. et al. | 128/706 |
| 3,939,824 | 2/1976 | Arneson et al. | 128/708 |
| 4,126,139 | 11/1978 | Walters et al. | 128/419 PG |
| 4,181,133 | 1/1980 | Kolenik et al. | 128/419 PG |
| 4,223,678 | 9/1980 | Langer et al. | 128/419 D |
| 4,248,244 | 2/1981 | Charnitski et al. | 128/706 |
| 4,280,502 | 7/1981 | Baker, Jr. et al. | 128/419 PG |

Primary Examiner—William E. Kamm
Assistant Examiner—Mitchell J. Shein
Attorney, Agent, or Firm—Robert C. Beck; John L. Rooney; Joseph F. Breimayer

[57] ABSTRACT

A pacer subsystem for detecting the existence of tachyarrhythmia including means for measuring the average time interval between successive heart beats and for comparing a sample beat with both a percentage of this average, and with a preset time interval. If the sample beat period is less than both criteria, it is classified as a tachy beat. If the sample beat is longer than either time interval it is classified as a non-tachy beat. Sequences of tachy beats are used to initiate an appropriate therapeutic stimulation regime.

6 Claims, 7 Drawing Figures

TACHYARRHYTHMIA PACER

BACKGROUND OF THE INVENTION

1. Field of the Invention

This invention relates to implanted medical devices and is more particularly directed to a tachyarrhythmia detection system for incorporation into a pacemaker.

2. Description of the Prior Art

A variety of disease mechanisms may result in cardiac dysrhythmias. Typically, these dysrhythmias are characterized by electrical instability in the cardiac tissue which results in abnormal mechanical activity of the heart. The result of a dysrhythmia is typically the reduction in the rate at which oxygenated blood is circulated throughout the body. This parameter is called the cardiac output. If this loss of cardiac output results from a heartbeat slower than a normal heartbeat responding to the same physiological demand, the dysrhythmia is called a bradycardia. In contrast, an abnormally rapid beating of the heart which also results in reduced cardiac output is generically termed a pathologic tachycardia.

Early examples of pacemakers such as that taught by U.S. Pat. No. 3,478,746 to Greatbatch have been widely accepted as an appropriate therapy for bradycardias. These demand-type pacemakers provide a stimulus to the cardiac tissue through a catheter if no naturally occurring cardiac activity is sensed within a preset time period referred to as the escape interval. Consequently, stimulating pulses are supplied to the heart only when the intrinsic heart rate drops below a preset minimum rate corresponding to the escape interval.

Examples of prior art tachycardia treatment devices include the device taught by U.S. Pat. Nos. 3,698,398 and 3,693,627 to Berkovits. The teaching of these patents is directed primarily to the therapeutic stimulation applied to the heart after the detection of the tachyarrhythmia and each of these patents teach the use of a rate detection system for invoking the tachyarrhythmia treatment. Reliance on the use of detected depolarization rates of the cardiac tissue have been proposed in more recent examples of implantable tachyarrhythmia pacers including that taught by U.S. Pat. No. 4,181,133 to Kolenik, et al.

There are a number of problems associated with the use of these prior art rate detection systems for the detection of a pathologic tachyarrhythmia. One problem is that pathologic tachyarrhythmias can have rates within the range shared by normal heart activity. In effect, there is an overlap between physiologically normal and pathologic heart rates which reduces the effectiveness of a simple rate detection algorithm since it cannot reliably distinguish between the normal and the pathologic condition on rate data alone.

For these reasons, the rate threshold types of tachyarrhythmia detectors have proven inadequate to distinguish the pathologic tachyarrhythmia from related cardiac rhythms which do not require therapy. Consequently, pacers which rely on rate detectors alone have not been widely accepted for the treatment of tachyarrhythmia.

SUMMARY OF THE INVENTION

In contrast to the prior art, the arrhythmia detection system of the present invention measures the time period between successive cardiac depolarizations or beats and calculates an average time period or interval based upon a preselected number of beats. Each successive beat-to-beat interval is compared with this average. If the time period is longer than a preselected threshold time period then the beat is considered a normal beat. If the time interval is less than the average time interval by a preselected percentage and is also below an absolute period threshold, then the beat is classified as a tachy beat. Individual, paired and runs of multiple tachy beats may be accumulated and logged separately within the device.

The treatment regime of the pacer may be initiated after the number of successive tachy beats exceeds a preset threshold.

DETAILED DESCRIPTION OF THE PREFERRED EMBODIMENT

Figure 1:
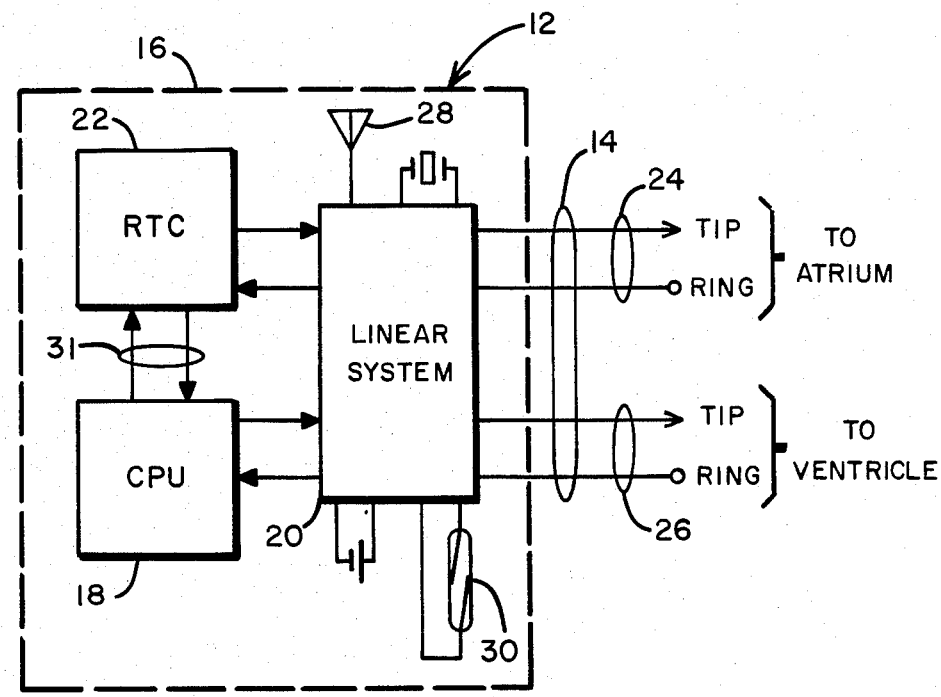
FIG. 1 is a block diagram showing the functional organization of a tachyarrhythmia pacer incorporating the present invention.

Turning to FIG. 1 there is shown a functional block diagram showing a pacer incorporating the present invention. The patient's heart is connected to the pacer shown generally as 12 through a lead system 14. The pacer includes a hermetic enclosure 16 and electronic subsystems. The pacer's electronic subsystems are partitioned into a central processing unit (CPU) 18, a real time controller (RTC) 22, and a linear system 20.

In general, the linear system provides the electrical interface with the heart and includes an atrial sense amplifier and atrial output stage connected to atrial lead pair 24. Likewise, a ventricular sense amplifier and ventricular output amplifier are connected to ventricular lead pair 26. Examples of circuitry suitable for these purposes may be found in U.S. Pat. No. 4,266,551 to Stein and U.S. patent application Ser. No. 957,826 to Thompson, which are incorporated by reference.

Additional functions which may be incorporated in the linear system 20 include telemetry reception and transmission circuitry to permit non-invasive communication with the implanted pacer. In this connection an antenna 28 and magnetic reed switch 30 are provided. Examples of telemetry systems suitable for use in this invention include U.S. Pat. No. 3,833,005 to Wingrove; U.S. Pat. No. 4,055,086 to Adams and Alferness and U.S. patent application Ser. No. 194,807 (Thompson) which are incorporated by reference.

The CPU subsection is an eight-bit parallel processor which includes volatile and non-volatile memories. This subsection is described further in U.S. patent application Ser. No. 112,591 to McDonald, et al. The CPU communicates with the RTC through a multiplexed address/data bus 31. The instruction set of the CPU is similar to an Intel 8085 microprocessor which is a commercially available device.

The RTC includes a number of eight-bit count-down timers, and a serial eight-bit I/O part. An interrupt controller with eight priorities and eight vectored interrupts is also provided.

The multi-chip system described above constitutes the architecture of the pacer which incorporates the tachy detection system of the present invention.

The pacer may operate in any of the known pacing modes including the dual demand mode, atrial ventricular sequential mode, atrial synchronous ventricular inhibited mode, and the ventricular demand mode in addition to known tachy treatment modes. In this context the present invention may be regarded as subsystem of the pacer which involves the treatment of tachyarrhythmia and more particularly, is directed to the detection of tachyarrhythmia.

Figure 2:
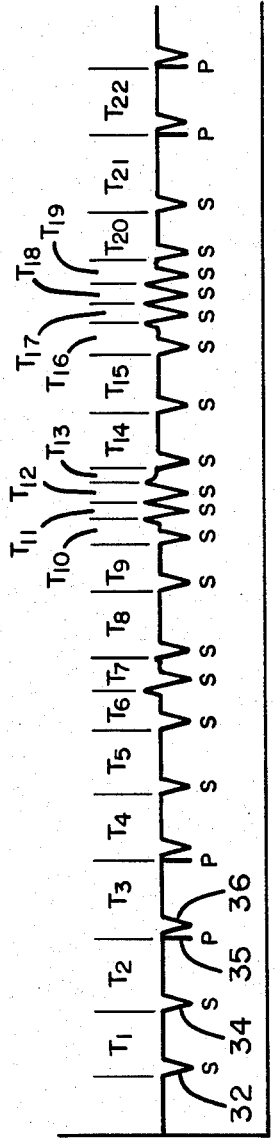
FIG. 2 is a hypothetical electrogram as measured by the implanted tachyarrhythmia pacer.

Turning to FIG. 2, there is shown an electrogram as measured in a ventricle of the patient's heart. In this somewhat stylized representation the downward deflections, as typified by waveform complex 32, are representations of the depolarization of the ventricular tissues of the heart. The time period between successive depolarizations, shown for example between 32 and 34, are measured through timer means located within the RTC logic 22. The time periods labeled T-1 through T-22 represent the measured time periods between the successive cardiac depolarizations shown in the figure. In the diagram, cardiac events sensed by the sense amplifiers, which were not stimulated by the pacemaker are labeled with an "S" below the associated complex. Paced events typified by complex 36 are labeled with a "P" to indicate that the pacing stimulus shown by the waveform spike 35, initiated the cardiac depolarization. The information collected by the logic for use in the detection of a tachyarrhythmia includes sensed-to-sensed time periods and paced-to-sensed time periods and does not include time periods extending from a sensed event to a paced event or time period extending from a paced event to paced event. As a consequence of this criteria time periods T-2, T-3, T-22 would be excluded from the tachyarrhythmia detection procedure. However, all other time periods shown in FIG. 2 would be utilized to ascertain the existence of tachy episodes.

Figure 3:
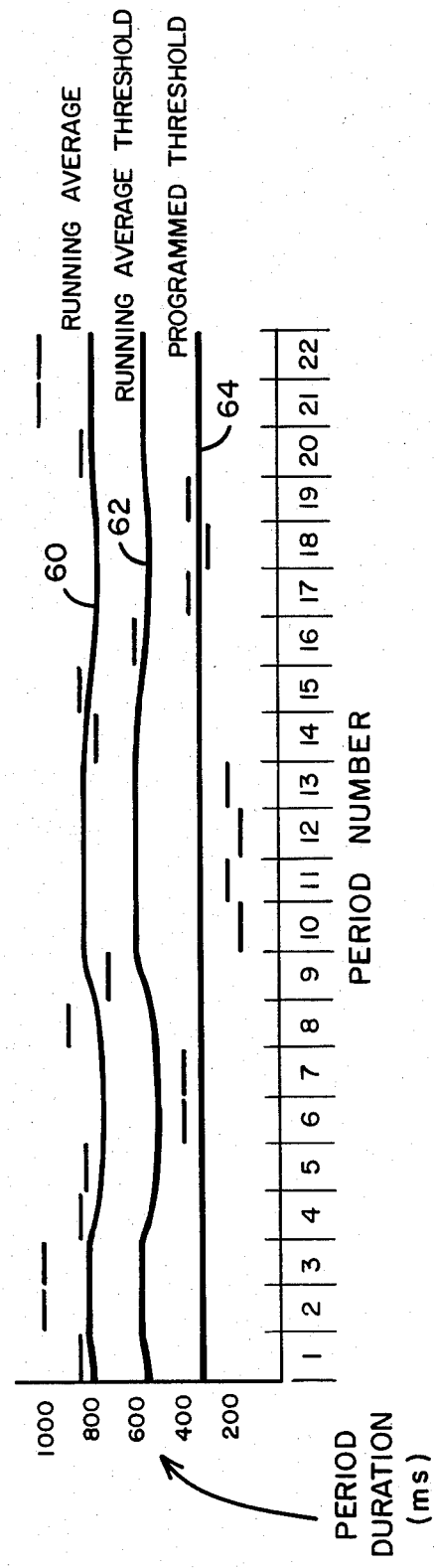
FIG. 3 is a graph showing the time period variations of the electrogram information shown in FIG. 2.

Referring to FIG. 3, the information in FIG. 2 is shown in a different format. The ordinate represents the time period between successive sensed-to-sensed or paced-to-sensed events. The abscissa indicates the time period number. For example, the time period T-1 shown in FIG. 2 is represented by the bar above location 1 of the FIG. 3 diagram.

In operation each successive cardiac depolarization is classified as a tachy or a non-tachy beat. For a period to be classified as a tachy beat it must meet two criteria. The first criteria is, a fixed programmable value labeled "Programmed Threshold" 63 on FIG. 3. The second criteria is a fixed programmable percentage of a four-period running average of the preceding non-tachy beats. This criteria is labeled "Running Average Threshold" 62 on FIG. 3. It is important to note that the running average calculation includes only sensed-to-sensed beat intervals and paced-to-sensed beat intervals and excludes sensed-to-paced intervals as well as paced-to-paced intervals.

Referring again to FIG. 3, the time periods T-1, T-3, T-4 and T-5 have been averaged and represented by the line 60. A programmable percentage threshold value is shown by line 62 and is equal to approximately 50% of the average time period. The programmable rate threshold indicated by line 64 is set to a time period corresponding to approximately 350 milliseconds. Thus the beats corresponding to the time period T-10, T-11, T-12, T-13 and T-18 fall both below the programmable percentage threshold as well as the absolute threshold.

A further distinction is made between the classified tachy beats. For example, it should be noted from FIG. 3 that the tachy beat T-18 stands alone and is not a member of a run of tachy beats. In contrast, the time periods and beats labeled T-10, T-11, T-12 and T-13 form a run of four tachy beats in a row. Typically memory locations in the CPU are allocated to store the number of occurrences of runs of tachy beats. It is presently contemplated that these memory locations or "bins" will separately log single occurrence tachy beats, paired tachy beats and runs three or more tachy beats. Some selected pacer therapies may be selected in response only to extended runs of tachy beats.

Telemetry means may be provided to permit the attending physician to interrogate the pacemaker and access logged data which relates to the numbers of sequential tachy beats in each bin, and to alter the Running Average Threshold and Programmable Threshold, detection criteria.

As previously described the detection criteria includes a "Running Average Threshold" and a "Programmed Threshold." It is presently contemplated that the physician will be able to non-invasively program five discrete "Running Average Threshold" corresponding to a 12.5%, 25%, 37.5%, 50%, and 62.5% reduction in the beat-to-beat time period. Likewise, the "Programmed Threshold" will be programmable from 200 to 600 milliseconds in 50 millisecond intervals.

Figure 4:
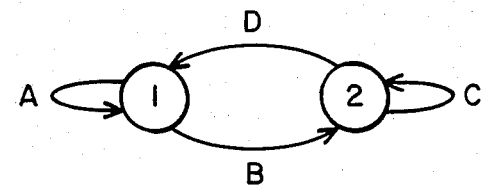
FIG. 4 is a state diagram describing the operation of the tachyarrhythmia detection system.
Figure 5:
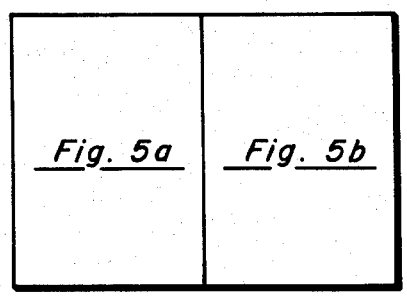
FIG. 5 is a diagram depicting the proper association between FIGS. 5a and 5b.

Turning to FIG. 4, there is a state diagram representation for the detection system. The first state may be called the idling state while the second state may be called the enumerating state. State transition A updates the running average of the time period thus providing a numerical value for the average time period and also turns off the tachy flag which is used to invoke the tachyarrhythmia treatment. The state transition from state 1 to state 2 indicated by transition B performs a reset of the consecutive period counter to 1 and is driven through the occurrence of a detected tachy beat. In enumerating state 2 the transition C is driven by an additional occurrence of a tachy beat and this increments the consecutive period counter by 1, and turns the tachy flag on at a counter value of 5. The state transition from state 2 to state 1 indicated by transition D occurs after a paced event or the detection of a non-tachy beat. This transition updates the bin counter and if a bin is full the machine is turned off. This transition additionally moves the machine from state 2 to state 1.

It is well known that electronic systems represented by state diagrams may be implemented either in hardware or in software.

Figure 5A:
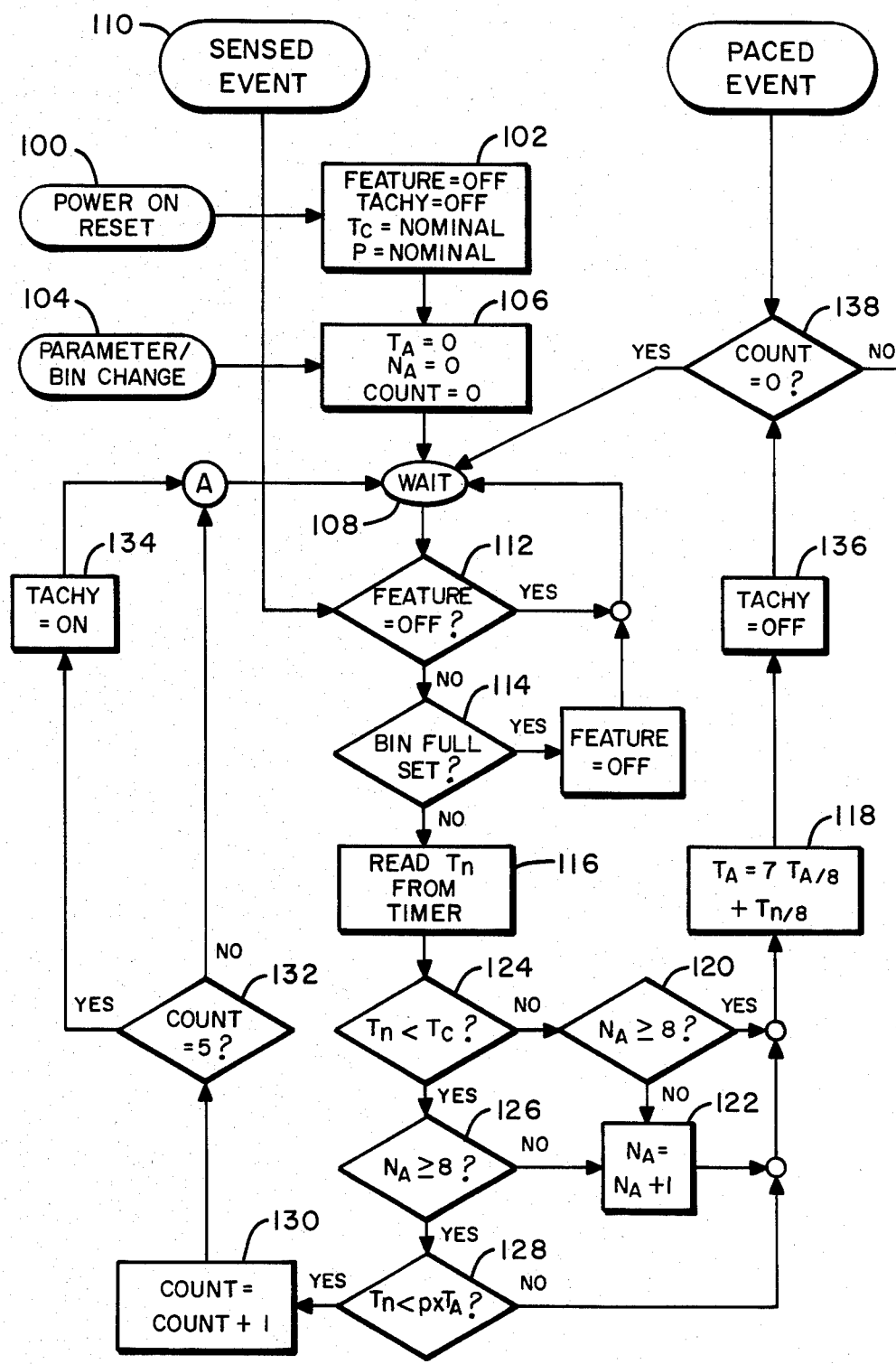
FIGS. 5a and 5b are a flow chart representation of a software implementation of the tachyarrhythmia detection system.
Figure 5B:
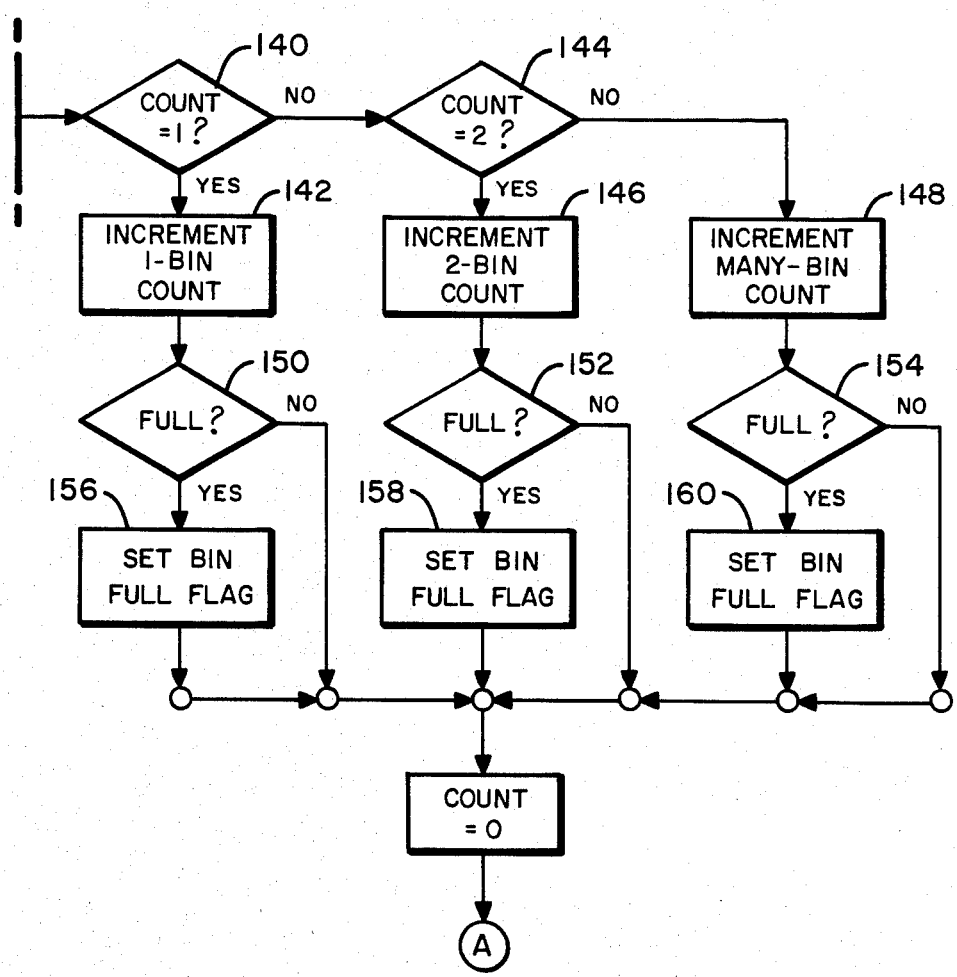

It is presently contemplated that the tachyarrhythmia detection system of the present invention will be implemented in software. FIGS. 5a and 5b are a flow chart of a software implementation.

The tachyarrhythmia detection system is initialized by a power on reset indicated in the flow chart by element 100. When battery voltage is first applied to the circuitry or when the battery recovers from a low voltage condition, the arrhythmia detection feature is disabled and the tachycardia therapy (tachy) is disabled and the running average percent threshold are set to nominal values. Turning the detection feature off as well as the tachy treatment off, as indicated by element 102, ensures that no unwanted processing or therapy occurs during the power up condition. Additionally, it places the arrhythmia detection and the tachy therapy systems into a known state. By presetting the running average percent threshold and program threshold to nominal values circumvents operational and indeterminancy problems arising if the feature was activated but the values for these parameters were not currently supplied. Alternatively, one could prevent the feature from being turned on until parameter values had been supplied, however the additional computational burden associated with this operational mode is regarded as too complex for a power-constrained data processing system.

After the initialization routine the nominal parameters may be altered through noninvasive programming and the bin counts may be zeroed by telemetered data from a remote transmitter. This sequence is indicated on the flow chart by element 104. Additionally, the running average is set to zero as is the number of non-tachy beats. This is indicated by element 106 in the flow chart.

After this preliminary programming the tachyarrhythmia detection feature of the present invention is enabled and will wait until certain real time events occur as indicated by element 108. The real time events which drive the tachyarrhythmia detection feature as explained in connection with the state diagram are the occurrence of sensed and paced events. The occurrence of a sensed event resulting from a sensed sense time interval or pace-to-sense time interval causes the entry into decision element 112. If the tachyarrhythmia detection feature is programmed to the off condition the process is halted at element 108. If the arrhythmia detection feature is on, decision block 114 is entered. If it is determined that a bin has been filled due to the last bin update, the arrhythmia detection feature is turned off and again the process is halted. However, if the feature is on and no bins have been filled element 116 is entered. The time of the intrinsic cardiac cycle is measured and read into element 116. If the measured period is longer than the programmable threshold period the measured period is entered into element 118 with appropriate updates to the beat counter designated by elements 120 and 122. This sequence may be termed "the occurrence of a non-tachy event." If, on the other hand, decision block 124 determines that the intrinsic or measured time period is less than the threshold period, then a condition for a tachy beat period is satisfied and the process moves to element 126.

In element 126 the integrity of the value of the running average is tested by testing whether or not eight intervals are contained in the average. If there are not eight intervals in the average the counter is incremented in element 122 and the current value of the intrinsic beat is included in this running average. If there are eight intervals included in the value of the running average, the process continues to the step represented by decision element 128. In decision block element 128, the second condition for a tachy period is tested. If the measured time interval is less than a programmed percentage of the average time, then the interval is judged a tachy beat and the process continues to element 130. If the measured time intervals fails this test, then the process updates the running average in element 118.

If the interval is determined to be a tachy beat the counter of consecutive tachy periods is incremented in element 130. If this count equals five, the tachy therapy is enabled in element 134.

It is important to note that the value of a beat which is determined to be a tachy beat is not included in the running average. This, of course, is due to the fact that the running average is defined as the average value of the non-tachy cycle periods.

If an intrinsic time interval is judged to be non-tachy either by failing one of the criteria or if it was terminated by a paced event, a test is made in element 138 concerning the number of consecutive tachy beats which have occurred prior to this particular non-tachy interval. If the value is zero, the process halts in element 108. If, however, the value of count as determined by element 138 is greater than zero, at least one tachy beat has just occurred prior to this cardiac cycle. The processes indicated by elements 140 and 142 count the number of singularly occurring tachy beat while processes indicated by elements 144 and 146 count the number of paired tachy beats and the process indicated by element 148 counts those strings of tachy beats involving more than two consecutive intervals. The processes associated with elements 150, 152 and 154 test for the counters or bins filling. If either the counters or bins are full the appropriate flags are set in elements 156, 158 and 160. The flags are tested by additional software upon the command of the attending physician through non-invasive telemetry to ascertain the number of events tallied in each of these counters.

Having thus described the invention, we claim:

1. In a pacer of the type having at least one sense amplifier for detecting depolarization of cardiac tissue and, at least one output amplifier for providing electrical stimulation to the cardiac tissue; an improved tachyarrhythmia detection system comprising:
   timing means for determining time periods between successive cardiac depolarizations;
   averaging means for calculating the average time period for a preselected number of said time periods producing a running average period;
   means for calculating a running average threshold period from said running average period;
   means for comparing a time period with said running average threshold period producing a first criteria detection signal if said time period is less than or equal to said running average threshold period;
   means for comparing said time period to a preselected programmed threshold period and for producing a second criteria detection signal if said time period is less than or equal to programmed threshold period; and
   means responsive to said first and second criteria detection signals for incrementing a tachy beat counter; and
   means responsive to said tachy beat counter for initiating a tachyarrythmia treatment regime.

2. The device of claim 1 further including a telemetry system means for permitting the non-invasive interrogation of said tachy beat counter.

3. The device of claim 2 wherein said telemetry system means further including means for the non-invasive alteration of said tachy beat counter.

4. The device of claim 2 wherein said telemetry system means permits the non-invasive alteration of said running average threshold period.

5. The device of claim 2 wherein said telemetry system means permits the non-invasive alteration of said programmed threshold period.

6. The device of claim 2 wherein said telemetry system means permits the non-invasive alteration of said preselected number of said time periods.

* * * * *